(12) United States Patent
Tonomura

(10) Patent No.: US 8,888,989 B2
(45) Date of Patent: Nov. 18, 2014

(54) METHOD AND APPARATUS FOR ELECTROLYTE MEASUREMENTS

(75) Inventor: Atsuro Tonomura, Akishima (JP)

(73) Assignee: JEOL Ltd., Tokyo (JP)

( * ) Notice: Subject to any disclaimer, the term of this patent is extended or adjusted under 35 U.S.C. 154(b) by 450 days.

(21) Appl. No.: 13/414,029

(22) Filed: Mar. 7, 2012

(65) Prior Publication Data

US 2012/0228158 A1     Sep. 13, 2012

(30) Foreign Application Priority Data

Mar. 10, 2011  (JP) ................... 2011-052399

(51) Int. Cl.
*G01N 27/416* (2006.01)
*G01N 27/403* (2006.01)
*G01N 27/333* (2006.01)

(52) U.S. Cl.
CPC ............ *G01N 27/403* (2013.01); *G01N 27/333* (2013.01); *G01N 27/4163* (2013.01)
USPC ............................ 205/789; 204/409; 204/416

(58) Field of Classification Search
CPC .................... G01N 27/416; G01N 27/4166
See application file for complete search history.

(56) References Cited

U.S. PATENT DOCUMENTS

| 5,288,374 A * | 2/1994 | Watanabe et al. ............. 205/779 |
| 2009/0194431 A1 * | 8/2009 | Ishibe .......................... 205/789 |

FOREIGN PATENT DOCUMENTS

| JP | 6109686 A | 4/1994 |
| JP | 200919960 A | 1/2009 |

* cited by examiner

*Primary Examiner* — Alex Noguerola
(74) *Attorney, Agent, or Firm* — The Webb Law Firm

(57) ABSTRACT

Method and apparatus to measure electrolytes. The apparatus has a measuring portion for measuring electromotive forces generated by a reference fluid and the sample fluid, respectively, by the use of an electrode portion. A dilution vessel for preparing the sample solution by diluting a sample fluid with a diluting fluid. A control portion for providing control such that the reference fluid and the sample solution are alternately supplied to the electrode portion from the dilution vessel and that a given amount of the diluting fluid is supplied to and wasted from the dilution vessel prior to the preparation of the sample solution.

8 Claims, 3 Drawing Sheets

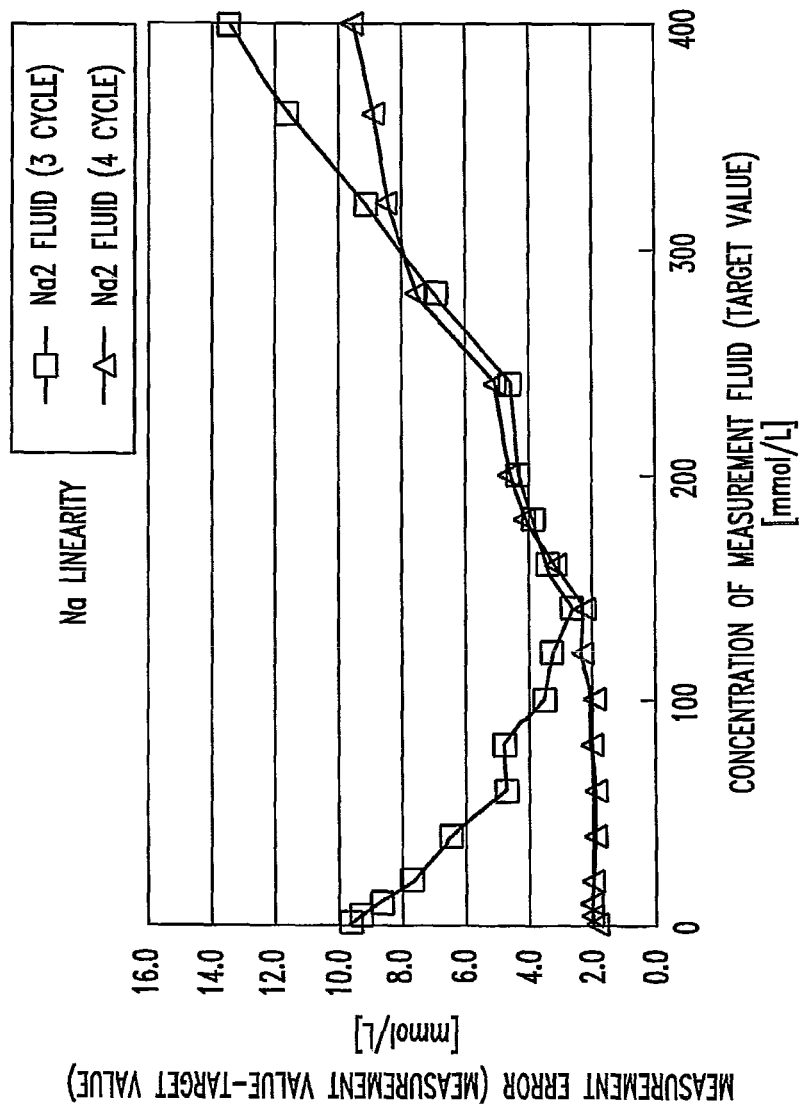

METHOD AND APPARATUS FOR ELECTROLYTE MEASUREMENTS

BACKGROUND OF THE INVENTION

1. Field of the Invention

The present invention relates to method and apparatus for performing measurements of the concentrations of electrolytes within solutions.

2. Description of Related Art

In recent years, ion sensors (especially, ion selective electrodes) have been actively applied to measurements in the medical field, and ions (e.g., sodium ions, potassium ions, and chlorine ions) dissolved in a sample such as blood or urine have been quantified.

Electrolyte measuring apparatus for measuring the concentrations of electrolytes (ionic concentration) within a sample such as urine or serum by the use of ion selective electrodes, i.e., apparatus employing a principle of measurement relying on ion selective electrodes, are known. Furthermore, a flow through analyzing system for measuring such plural ions at a time is available.

Such an electrolyte analyzer measures the electromotive force (i.e., the difference between the electric potential at one ion selective electrode and the electric potential at a reference electrode) produced by each sample through the use of the ion selective electrode (working electrode) and the reference electrode, measures the electromotive force produced by a reference fluid, and determines the concentration of the electrolyte of a measured component contained in the sample from measurement data obtained from the sample and reference fluid.

In the aforementioned electrolyte measuring apparatus utilizing the ion electrode method, a reference fluid and a sample are alternately measured in order to achieve stable electric potential measurements.

In this case, samples may be diluted with a buffer fluid prior to measurement in order to make uniform the samples in ionic strength and pH. At this time, the reference fluid that undergoes a measurement for comparison purposes is created using the same buffer fluid. A certain concentration of reference ions is contained in the reference fluid.

Two methods are conceivable as a method of adjusting the ion concentration of reference ions within the reference fluid. The first method is to use a reference fluid concentration lower than that of the diluted sample solution. The second method is to use a reference fluid concentration close to the concentration of the diluted sample solution.

With the first method, a reference fluid adjusted to a low concentration provides a reference for measurements. Besides, measurements can be made after diluting each sample with the reference fluid. Consequently, the diluting fluid and reference fluid can be unified. However, a great difference exists between the sample concentration and the reference fluid concentration and so if a temperature fluctuation occurs, the output electric potential varies greatly. Therefore, there is the problem that even if a temperature correction is made, variations among individual electrodes due to their temperature characteristics cannot be eliminated.

The relationship between the temperature fluctuation and the fluctuation in the output electric potential is found from the Nernst equation. It is known that the output electric potential tends to increase in proportion to temperature.

In contrast, when the reference fluid is adjusted close to the concentration of the sample solution by the second method, the sample solution and the reference fluid produce almost equal amounts of output electric potential fluctuation in response to temperature fluctuation because of the Nernst equation. Therefore, the measurement is less affected by temperature. There is the advantage that the measuring accuracy is unaffected by temperature. For this reason, the second method is often used in actual apparatus.

In the second method, however, the concentration of the reference fluid is higher than the concentration of the diluting fluid. Therefore, in a system configuration which produces a sample solution by mixing a sample and a diluting fluid in a dilution vessel, if carry-over of the reference fluid occurs within the dilution vessel, there may be the problem that the concentration of a sample solution to be measured next will increase.

Such an undesirable situation becomes conspicuous when the concentration of the sample solution has decreased. This presents the problem that the linearity of measurement results on the low concentration side of sample solutions deteriorates. Furthermore, this issue becomes more conspicuous when the amount of the sample volume has been reduced.

The decrease in the issue is determined by the nature and quantity of the reference fluid that is the carry-over in the dilution vessel and, therefore, the following countermeasures (1)-(3) have been taken heretofore.

(1) The dilution vessel where a sample is diluted is made separate from the path through which the reference solution is supplied.

(2) The reference fluid left in the dilution vessel where the fluid is drawn in by a nozzle.

(3) The relative amount of carry-over reference fluid is made negligible by increasing the amounts of the sample and diluting fluid without taking any of the countermeasures (1) and (2).

In JP-A-6-109686, it is proposed that the amount of diluting fluid is managed during dilution within the dilution vessel. However, any countermeasure to be taken when there is a carry-over of the reference fluid is not proposed at all.

In JP-A-2009-19960, an apparatus is proposed in which the paths for the sample solution and reference fluid are made separate from each other in the same way as in the countermeasure (1) above and in which the reference fluid does not pass through the dilution vessel where the sample is diluted with a diluting fluid. In this apparatus, carry-over of the reference fluid in the dilution vessel is avoided but there arises another problem that the piping layout is complicated, thus complicating the apparatus.

Furthermore, if the countermeasure (2) using a suction means for aspirating the carry-over of the reference fluid in the dilution vessel is taken, there arises the new problem that the instrument is complicated.

If the countermeasure (3) consisting of increasing the amount of the sample solution compared with the reference fluid to make negligible the effects of the reference fluid without varying the configuration is taken, a larger amount of sample is needed than heretofore. This creates the problems that the burden on the patient or subject under test increases and that this countermeasure cannot be carried out when the amount of the sample is small.

SUMMARY OF THE INVENTION

In view of the foregoing problems, the present invention has been made. It is an object of the invention to provide method and apparatus capable of precisely measuring electrolytes without complicating the configuration of the whole apparatus, without increasing the amount of a sample solution, and without relying on the concentration of the sample solution.

The present invention of the subject application that solves the foregoing problems can assume the following embodiments.

(1) The invention provides a method of measuring electrolytes by an electrolyte measuring apparatus having: a measuring portion for measuring electromotive forces generated by a reference fluid and a sample solution, respectively, by the use of an electrode portion having working electrodes and a reference electrode; a dilution vessel for preparing the sample solution by diluting a sample fluid with a diluting fluid; reference fluid supply means for supplying the reference fluid into the dilution vessel; diluting fluid supply means for supplying the diluting fluid into the dilution vessel; sample supply means for supplying the sample fluid into the dilution vessel; and measured fluid supplying means for supplying the reference fluid and the sample solution alternately to the electrode portion from the dilution vessel. When the reference fluid and the sample solution are alternately supplied to the electrode portion from the dilution vessel and measured, a given amount of the diluting fluid is supplied to and wasted from the dilution vessel prior to the preparation of the sample solution.

In this method of measurement of electrolytes, the following four steps are carried out in turn.

(1) The reference fluid is supplied to and wasted from the dilution vessel.

(2) The reference fluid is again supplied into the dilution vessel.

(3) The reference fluid is sent to the measuring portion from the dilution vessel and the resulting electromotive force is measured.

(4) The reference fluid is wasted from the dilution vessel.

Then, the following four steps are carried out in turn.

(5) The diluting fluid is supplied to and wasted from the dilution vessel.

(6) The diluting fluid and the sample fluid are supplied into the dilution vessel to prepare the diluted sample solution.

(7) The sample solution is sent to the measuring portion from the dilution vessel and the resulting electromotive force is measured.

(8) The sample solution is wasted from the dilution vessel.

(2) An electrolyte measuring apparatus of the present invention has: a measuring portion for measuring electromotive forces generated by a reference fluid and a sample solution, respectively, by the use of an electrode portion having working electrodes and a reference electrode; a dilution vessel for preparing the sample solution by diluting a sample fluid with a diluting fluid; sample supply means for supplying the sample fluid into the dilution vessel; diluting fluid supply means for supplying the diluting fluid into the dilution vessel; reference fluid supply means for supplying the reference fluid into the dilution vessel; measured fluid supply means for supplying the reference fluid and the sample solution to the electrode portion from the dilution vessel; and a control portion providing control such that the reference fluid and the sample solution are alternately supplied to the electrode portion from the dilution vessel and that a given amount of the diluting fluid is supplied to and wasted from the dilution vessel prior to the preparation of the sample solution.

In the inventive electrolyte measuring apparatus described thus far, the control portion controls the apparatus such that the following four steps are carried out in turn.

(1) The reference fluid is supplied to and wasted from the dilution vessel.

(2) The reference fluid is again supplied into the dilution vessel.

(3) The reference fluid is sent to the measuring portion from the dilution vessel and the resulting electromotive force is measured.

(4) The reference fluid is wasted from the dilution vessel.

Besides, the control portion controls the apparatus such that the following four steps are carried out in turn.

(5) The diluting fluid is supplied to and wasted from the dilution vessel.

(6) The diluting fluid and the sample fluid are supplied into the dilution vessel to prepare the sample solution.

(7) The sample solution is sent to the measuring portion from the dilution vessel and the resulting electromotive force is measured.

(8) The sample solution is wasted from the dilution vessel.

According to the invention configured as described so far, when the reference fluid and the sample solution are alternately supplied to the electrode portion from the dilution vessel and electromotive forces generated by the reference fluid and sample solution, respectively, are measured by the measuring portion, a given amount of the diluting fluid is supplied to and wasted from the dilution vessel prior to the preparation of the sample solution in the dilution vessel. Consequently, the effects of the reference fluid remaining in the dilution vessel and mixing with the sample solution can be reduced to a minimum. Therefore, in cases where the concentration of the reference ions within the reference fluid is close to the concentration of the sample or sample solution, the measuring accuracy can be prevented from deteriorating. That is, the electrolyte concentration can be precisely measured without complicating the configuration of the whole apparatus, without increasing the amount of the sample solution, and without recourse to the concentration of the sample solution.

BRIEF DESCRIPTION OF THE DRAWINGS

FIG. 3 is a graph illustrating the results of electrolyte measurements in accordance with one embodiment of the invention.

DESCRIPTION OF THE PREFERRED EMBODIMENTS

Embodiments of the present invention for implementing method and apparatus for measuring electrolytes are hereinafter described in detail with reference to the drawings.

<Configuration>

Figure 1:
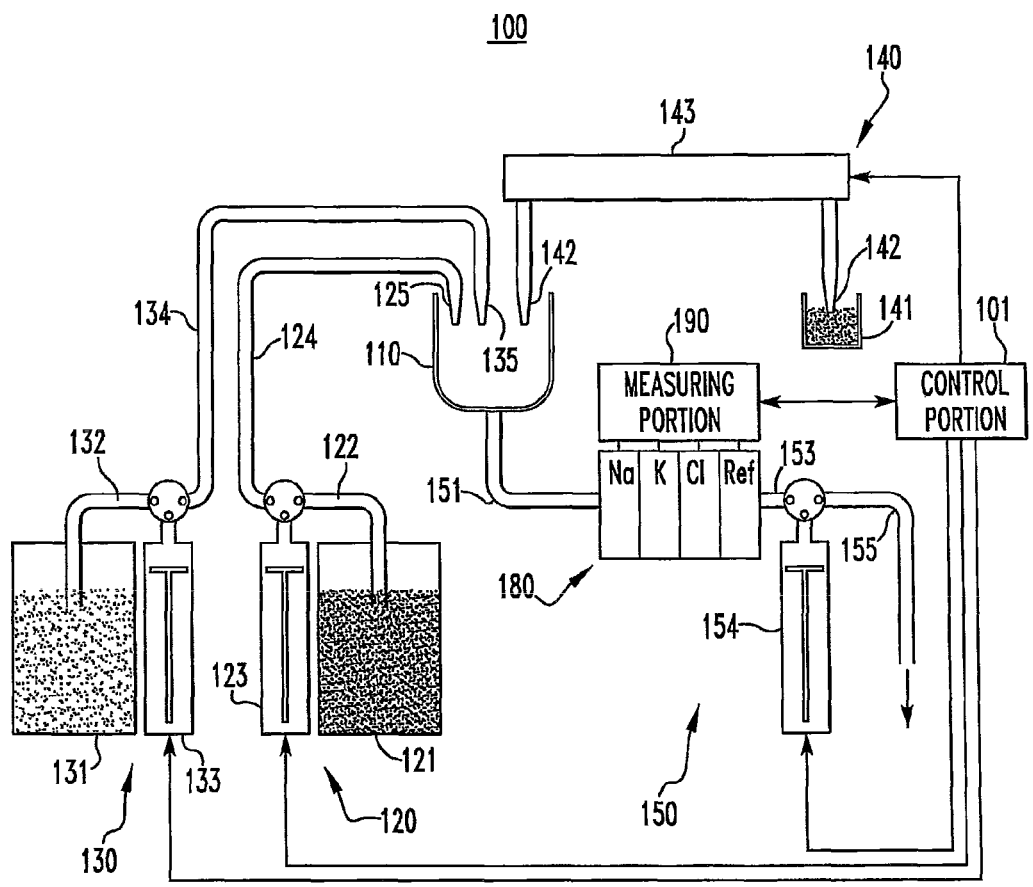
FIG. 1 is a schematic block diagram of an electrolyte measuring apparatus according to an embodiment of the present invention, showing its configuration.

The configuration of an electrolyte measuring apparatus, generally indicated by reference numeral 100, according to one embodiment of the present invention is first described by referring to FIG. 1.

In FIG. 1, known basic members, housing, and other parts which hold the electrolyte measuring apparatus 100 and its peripheral parts are omitted. Rather, the arrangement of the novel portions of the electrolyte measuring apparatus is mainly shown.

The electrolyte measuring apparatus 100 shown in FIG. 1 is configured mainly including a control portion 101 for controlling various portions of the apparatus, a dilution vessel 110 that is a container where a sample fluid is diluted with a diluting fluid to prepare a sample solution, diluting fluid supply means 120 for supplying the diluting fluid into the dilution vessel 110, reference fluid supply means 130 for supplying a reference fluid into the dilution vessel 110, sample supply means 140 for supplying the sample fluid into the dilution vessel 110, measured fluid supply means 150 for supplying the reference fluid and the sample solution alternately to an electrode portion 180 from the dilution vessel 110, and a measuring portion 190 for measuring electromotive forces produced in the electrode portion 180 in response to the reference fluid and the sample solution, respectively. The electrode portion 180 generates given electric potential differences between each working electrode and a reference electrode in response to the reference fluid and the sample solution, respectively.

The control portion 101 controls the various portions of the electrolyte measuring apparatus 100 using a CPU and a control program. During measurements, the control portion provides control such that a given amount of diluting fluid is supplied to and wasted from the dilution vessel 110 before a sample solution is prepared in the dilution vessel 110.

In the dilution vessel 110, the sample poured out from an aliquot dispensing nozzle 142 is diluted approximately 20-30 times with the diluting fluid poured out from a diluting fluid supply nozzle 125 and stirred uniformly by a stirring mechanism (not shown) to prepare a sample solution. This sample solution and a reference fluid poured out from a reference fluid supply nozzle 135 are alternately supplied to the electrode portion 180 from the dilution vessel 110 via the measured fluid supply means 150.

The diluting fluid supply means 120 is configured including a diluting fluid container 121 for accommodating the diluting fluid, a diluting fluid inlet pipe 122 for introducing the diluting fluid from the diluting fluid container 121, a pump 123 for drawing the diluting fluid out of the diluting fluid container 121 via the diluting fluid inlet pipe 122, a diluting fluid supply pipe 124 for supplying the diluting fluid pumped out of the pump 123 toward the dilution vessel 110, and the diluting fluid supply nozzle 125 for pouring out the diluting fluid pumped out from the pump 123 toward the dilution vessel 110.

The reference fluid supply means 130 is configured including a reference fluid container 131 for accommodating the reference fluid, a reference fluid inlet pipe 132 for introducing the reference fluid from the reference fluid container 131, a pump 133 for drawing the reference fluid out of the reference fluid container 131 via the reference fluid inlet pipe 132, a reference fluid supply pipe 134 for supplying the reference fluid pumped out of the pump 133 toward the dilution vessel 110, and the reference fluid supply nozzle 135 for pouring out the reference fluid pumped out of the pump 133 toward the dilution vessel 110. The concentration of the reference ions within the reference fluid is close to either the concentration of a diluted sample or the concentration of the sample solution.

The sample supply means 140 is configured including a sample container 141 for accommodating a sample, the aliquot dispensing nozzle 142 for supplying a given amount of sample (aliquot) from the sample container 141 into the dilution vessel 110, and a nozzle drive portion 143 for controlling motion of the nozzle 142 and drawing and delivery of aliquots of sample.

The measured fluid supply means 150 is configured including a measured fluid supply pipe 151 for supplying a measured fluid (i.e., the sample solution or reference fluid from the dilution vessel 110) to the electrode portion 180, a waste fluid pipe 153 for wasting the fluid undergone a measurement in the electrode portion 180 as a waste fluid, a pump 154 for supplying the measured fluid to the electrode portion 180 and drawing out the measured fluid undergone the measurement as a waste fluid via the waste fluid pipe 153, and a waste fluid pipe 155 permitting the waste fluid pumped out of the pump 154 to the outside.

The electrode portion 180 is configured including working electrodes (ion selective electrodes) for Na, K, and Cl, respectively, as shown in FIG. 1 and a reference electrode (Ref). As each of the measured fluids (sample solution and reference fluid) passes across the electrode portion, a given electric potential difference corresponding to the electrolyte concentration is developed between the potential at each of the working electrodes and the electric potential at the reference electrode. Each of the working electrodes develops an electric potential in response to a certain type of ions such as Na (sodium) ions, K (potassium) ions, or Cl (chlorine) ions.

The measuring portion 190 measures the given electric potential difference developed between the potential at each working electrode and the potential at the reference electrode in response to the electrolyte concentration for each of the sample solution and the reference fluid. Furthermore, the measuring portion calculates the electrolyte concentrations such as of Na (sodium) ions, K (potassium) ions, and Cl (chlorine) ions according to the potential differences. Preferably, the potential at the electrode portion 180 is stabilized by electrically grounding the metal portion of the measured fluid supply pipe 151 at a reference potential in an unillustrated manner, the pipe 151 acting to supply the reference fluid and the sample solution alternately to the electrode portion 180.

<Operation>

The operation of the electrolyte measuring apparatus 100 to implement the method of measuring the electrolyte concentrations of the measured components within the sample solution is described.

First, if an instruction for starting a measurement is issued (YES at step S101 of FIG. 2), the control portion 101 starts the following measuring operation.

Cleaning with Reference Fluid

The pump 133 is driven under control of the control portion 101 to draw in the reference fluid from the reference fluid container 131 via the reference fluid inlet pipe 132 and via the reference fluid supply pipe 134. A given amount of the reference fluid is poured out into the dilution vessel 110 from the reference fluid supply nozzle 135. Similarly, the stirring mechanism (not shown) is driven under control of the control portion 101 to clean the inside of the dilution vessel 110 with the reference fluid. The pump 154 is driven under control of the control portion 101 to draw in the reference fluid, which was used for the cleaning, from inside the dilution vessel 110. The fluid is then wasted to the outside via the waste fluid pipes 153 and 155 (step S102 of FIG. 2.)

Measurement of Reference Fluid

Then, the pump 133 is driven under control of the control portion 101 to draw in the reference fluid from the reference fluid container 131 via the reference fluid inlet pipe 132 and via the reference fluid supply pipe 134. A given amount of the reference fluid is poured out into the dilution vessel 110 from the reference fluid supply nozzle 135 (step S103 of FIG. 2).

The pump 154 is driven under control of the control portion 101. The reference fluid flows as the measured fluid through the measured fluid supply pipe 151 and reaches the electrode portion 180. When the reference fluid passes through the electrode portion 180 including the working electrodes and the reference electrode, the measuring portion 190 measures the electromotive forces generated by the reference fluid through the working electrodes and the reference electrode (step S104 of FIG. 2). A notice of the electromotive forces measured by the measuring portion 190 in this way is given to the control portion 101. The measured reference fluid is drawn in by driving the pump 154 under control of the control portion 101 and wasted to the outside via the waste fluid pipes 153 and 155 (step S105 of FIG. 2).

Cleaning with Diluting Fluid

The pump 123 is driven under control of the control portion 101 to draw in the diluting fluid from the diluting fluid container 121 via the diluting fluid inlet pipe 122 and via the diluting fluid supply pipe 124 and to deliver a given amount of diluting fluid into the dilution vessel 110 from the diluting fluid supply nozzle 125. Similarly, the stirring mechanism (not shown) is driven under control of the control portion 101 to clean the inside of the dilution vessel 110 with the diluting fluid in order to reduce the effects of the carry-over of the immediately used reference fluid. Alternatively, the inside may not be cleaned; the diluting fluid may be simply supplied into the dilution vessel 110 and then poured out. The pump 154 is driven under control of the control portion 101 to draw in the diluting fluid, which was used for the cleaning, from inside the dilution vessel 110 and wasted to the outside via the waste fluid pipes 153 and 155 (step S106 of FIG. 2).

Measurement of Sample Solution

The pump 123 is then driven under control of the control portion 101 to draw in the diluting fluid from the diluting fluid container 121 via the diluting fluid inlet pipe 122 and via the diluting fluid supply pipe 124 and to deliver a given amount of diluting fluid necessary to prepare a sample solution into the dilution vessel 110 from the diluting fluid supply nozzle 125.

An aliquot of the sample held in the sample container 141 is taken by the aliquot dispensing nozzle 142 under control of the control portion 101. The sample aliquot is delivered into the dilution vessel 110 in which the diluting fluid has been poured out. Consequently, the sample is diluted at a given ratio by the diluting fluid, and a sample solution for a measurement is prepared (step S107 of FIG. 2).

The sample solution prepared by the dilution vessel 110 in this way is drawn in by the operation of the pump 154, passes through the measured fluid supply tube 151 as a measured fluid, and reaches the electrode portion 180. When the sample solution passes through the electrode portion 180 including the working electrodes and reference electrode, the measuring portion 190 measures the electromotive force generated by the sample solution through the working electrodes and reference electrode (step S108 of FIG. 2). A notice of the electromotive force measured by the measuring portion 190 in this way is given to the control portion 101.

The sample solution undergone the measurement is drawn in and passed through the electrode portion 180 by the continued operation of the pump 154. The solution is wasted to the outside as a waste fluid through the waste fluid pipes 153 and 155 (step S109 of FIG. 2).

Figure 2:
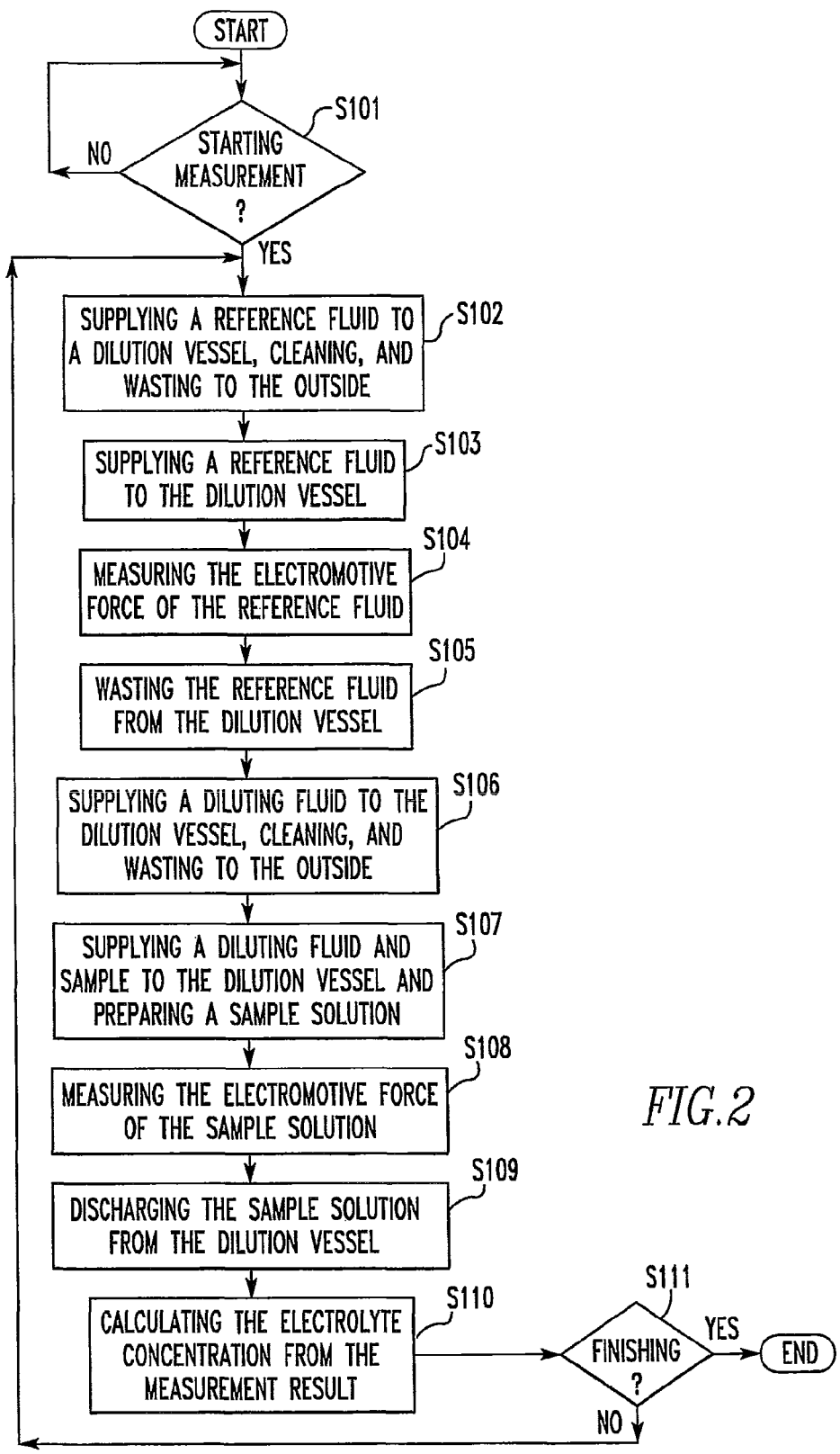
FIG. 2 is a flowchart illustrating a procedure for measuring an electrolyte in accordance with one embodiment of the invention.

The control portion 101 calculates the electrolyte concentration based on data about the electromotive forces generated by the reference fluid and sample solution which are measured by the measuring portion 190 and of which notice has been given (step S110 of FIG. 2). The control portion displays the calculated electrolyte concentration on a display portion (not shown) or gives a notice of the concentration to other device (not shown).

Ensuing Operations

The control portion 101 makes a decision as to whether ensuing measurements are necessary or this sequence of measurements should be terminated (step S111 of FIG. 2). If the decision is that ensuing measurements are necessary (NO at step S111 of FIG. 2), cleaning of the dilution vessel 110 with the reference fluid (step S102 of FIG. 2), measurement of the reference fluid (steps S103-S105 of FIG. 2), cleaning of the dilution vessel 110 with the diluting fluid (step S106 of FIG. 2), measurement of the sample solution (steps S107-S109 of FIG. 2), and calculation of the electrolyte concentration from the results of the measurement of the reference fluid and from the results of the measurement of the reference fluid (step S110 of FIG. 2) are repeated.

Terminating Operation

Furthermore, the control portion 101 makes a decision as to whether ensuing measurements are necessary or this sequence of measurements should be terminated (step S111 of FIG. 2). If the decision is that the sequence should be terminated (YES at step S111 of FIG. 2), this sequence of processing is terminated. The control portion 101 executes various known processing steps concomitant with the end.

According to this embodiment, when a reference fluid and a sample solution are alternately supplied to the electrode portion 180 from the dilution vessel 110 and electromotive forces produced by the reference fluid and sample solution, respectively, are measured by the measuring portion 190, a given amount of the diluting fluid is supplied to and wasted from the dilution vessel 110 to thereby clean it prior to the preparation of the sample solution in the dilution vessel 110. Consequently, the effects of the carry-over of the reference fluid existing in the dilution vessel 110 and mixing in the sample solution can be reduced to a minimum. Therefore, in a case where the concentration of the reference ions in the reference fluid is close to the concentration of the sample or to the concentration of the sample solution, the measuring accuracy can be prevented from deteriorating. That is, according to the present embodiment, the electrolyte concentration can be precisely measured without complicating the configuration of the whole apparatus, without increasing the amount of the sample solution, and without relying on the concentration of the sample solution.

Specific measurements were made by a conventional technique. Also, specific measurements were made according to the present embodiment. The results are shown in FIG. 3. In the graph of FIG. 3, the vertical axis indicates the concentration of Na (target value) of a sample solution in milli mol/L. The vertical axis indicates the results of the measurements (i.e., measurements of Na of the sample solution (milli mol/L)−target value of Na (milli mol/L), denoting a measurement error. Therefore, the values on the vertical axis are preferably closer to 0.

In the conventional techniques, each measurement was made on two fluids with three cycles. That is, cleaning of a reference fluid, measurement of the reference fluid, and measurement of a sample solution. In the present embodiment, each measurement was made on two fluids with four cycles. That is, cleaning of a reference fluid, measurement of the reference fluid, cleaning with a diluting fluid, and measurement of a sample solution.

In the results of the measurements made with the conventional techniques using the three cycles shown in FIG. 3, as the sample solution concentration decreased away from 140 milli mol/L, the effects of the carry-over of the reference fluid in concentrations higher than the sample solution became more strongly. It can be seen that the measuring error gradually increased.

On the other hand, in the present embodiment using the four cycles shown in FIG. 3, the cleaning step using a diluting fluid was effected prior to the measurement of the sample solution. Therefore, as the sample solution concentration decreased away from 140 milli mol/L, the carry-over of the reference fluid in concentrations higher than the sample solution produced no effects. The measuring error remained small over a wide range of concentrations.

That is, according to the present embodiment, electrolyte concentrations can be precisely measured without complicating the configuration of the whole apparatus, without increasing the amount of the sample solution, and without relying on the concentration of the sample solution.

Having thus described my invention with the detail and particularity required by the Patent Laws, what is desired protected by Letters Patent is set forth in the following claims.

The invention claimed is:

1. A method of measuring electrolytes by an electrolyte measuring apparatus having:
    a measuring portion for measuring electromotive forces generated by a reference fluid and a sample solution, respectively, by the use of an electrode portion having working electrodes and a reference electrode;
    a dilution vessel for preparing the sample solution by diluting a sample fluid with a diluting fluid;
    reference fluid supply means for supplying the reference fluid into the dilution vessel;
    diluting fluid supply means for supplying the diluting fluid into the dilution vessel;
    sample supply means for supplying the sample fluid into the dilution vessel; and
    measured fluid supply means for supplying the reference fluid and the sample solution alternately to the electrode portion from the dilution vessel;
    comprising two processes each including four steps performed in turn:
        (1) causing the reference fluid to be supplied to and wasted from the dilution vessel,
        (2) supplying the reference fluid again into the dilution vessel,
        (3) sending the reference fluid to the measuring portion from the dilution vessel and measuring the resulting electromotive force,
        (4) wasting the reference fluid from the dilution vessel,
        (5) causing the diluting fluid to be supplied to and wasted from the dilution vessel,
        (6) supplying the diluting fluid and the sample fluid into the dilution vessel to prepare a sample solution,
        (7) sending the sample solution to the measuring portion from the dilution vessel and measuring the resulting electromotive force, and
        (8) wasting the sample solution from the dilution vessel,
    wherein, when the reference fluid and the sample solution are alternately supplied to the electrode portion and measured, a given amount of the diluting fluid is supplied to and wasted from the dilution vessel prior to the preparation of the sample solution.

2. A method of measuring electrolytes as set forth in claim 1, wherein when the reference fluid and the sample solution are alternately supplied to the electrode portion and measured, a given amount of the reference fluid is supplied to and wasted from the dilution vessel prior to the measurement of the reference fluid.

3. A method of measuring electrolytes as set forth in claim 1, wherein the diluting fluid is supplied to and wasted from the dilution vessel prior to the preparation of the sample solution after the reference fluid has passed through the dilution vessel in order to perform measurements in the measuring portion.

4. A method of measuring electrolytes as set forth in claim 3, further comprising the step of causing the reference fluid to be supplied to and wasted from the dilution vessel prior to the measurement of the reference fluid after the sample solution has passed through the dilution vessel in order to perform measurements in the measuring portion.

5. An electrolyte measuring apparatus comprising:
    a measuring portion for measuring electromotive forces generated by a reference fluid and a sample solution, respectively, by the use of an electrode portion having working electrodes and a reference electrode;
    a dilution vessel for preparing the sample solution by diluting a sample fluid with a diluting fluid;
    reference fluid supply means for supplying the reference fluid into the dilution vessel;
    diluting fluid supply means for supplying the diluting fluid into the dilution vessel;
    sample supply means for supplying the sample fluid into the dilution vessel;
    measured fluid supply means for supplying the reference fluid and the sample solution to the electrode portion from the dilution vessel; and
    a control portion providing control such that the reference fluid and the sample solution are alternately supplied to the electrode portion from the dilution vessel and that a given amount of the diluting fluid is supplied to and wasted from the dilution vessel prior to the preparation of the sample solution,
    wherein said control portion provides means for instructing two processes each including four steps performed in turn:
        (1) causing the reference fluid to be supplied to and wasted from the dilution vessel,
        (2) supplying the reference fluid again into the dilution vessel,
        (3) sending the reference fluid to the measuring portion from the dilution vessel and measuring the resulting electromotive force,
        (4) wasting the reference fluid from the dilution vessel,
        (5) causing the diluting fluid to be supplied to and wasted from the dilution vessel,
        (6) supplying the diluting fluid and the sample fluid into the dilution vessel to prepare the sample solution,
        (7) sending the sample solution to the measuring portion from the dilution vessel and measuring the resulting electromotive force, and
        (8) wasting the sample solution from the dilution vessel.

6. The electrolyte measuring apparatus of claim 5, wherein said control portion further provides means for instructing a given amount of the reference fluid to be supplied to and wasted from the dilution vessel prior to the measurement of the reference fluid when the reference fluid and the sample solution are alternately supplied to the electrode portion and measured.

7. The electrolyte measuring apparatus of claim 5, wherein said control portion provides means for instructing the diluting fluid to be supplied to and wasted from the dilution vessel prior to the preparation of the sample solution after the reference fluid has passed through the dilution vessel in order to perform measurements in the measuring portion.

8. The electrolyte measuring apparatus of claim 7, wherein said control portion further provides means for instructing the reference fluid to be supplied to and wasted from the dilution vessel prior to the measurement of the reference fluid after the sample solution has passed through the dilution vessel in order to perform measurements in the measuring portion.

* * * * *